US012706188B2

(12) United States Patent
Nadler et al.

(10) Patent No.: US 12,706,188 B2
(45) Date of Patent: Aug. 11, 2026

(54) MEDICAL QUESTION ANSWERING SYSTEM

(71) Applicant: Xyla Inc., Wilmington, DE (US)

(72) Inventors: Daniel Joseph Nadler, Nassau (BS); Zachary Michael Ziegler, Cambridge, MA (US); Jonas Sebastian Wulff, Los Angeles, CA (US); Evan Michael Hernandez, Wimauma, FL (US); Eric Lehman, Boston, MA (US); Micah Smith, Boston, MA (US)

(73) Assignee: OpenEvidence Inc., Miami, FL (US)

( * ) Notice: Subject to any disclaimer, the term of this patent is extended or adjusted under 35 U.S.C. 154(b) by 0 days.

(21) Appl. No.: 18/975,915

(22) Filed: Dec. 10, 2024

(65) Prior Publication Data

US 2026/0080986 A1 Mar. 19, 2026

Related U.S. Application Data

(60) Provisional application No. 63/695,309, filed on Sep. 16, 2024.

(51) Int. Cl.

| | |
|---|---|
| ***G16H 70/20*** | (2018.01) |
| ***G06N 3/0475*** | (2023.01) |
| ***G16H 10/60*** | (2018.01) |

(52) U.S. Cl.
CPC .......... *G16H 10/60* (2018.01); *G06N 3/0475* (2023.01); *G16H 70/20* (2018.01)

(58) Field of Classification Search
None
See application file for complete search history.

(56) References Cited

U.S. PATENT DOCUMENTS

| | | | | |
|---|---|---|---|---|
| 10,303,798 B2 | 5/2019 | Stubley et al. | | |
| 2011/0270843 A1* | 11/2011 | Albin | G06F 16/951 707/769 | |

(Continued)

FOREIGN PATENT DOCUMENTS

| | | |
|---|---|---|
| JP | 2005-190055 A | 7/2005 |
| JP | 2019-125240 A | 7/2019 |

(Continued)

OTHER PUBLICATIONS

Hussain, M., Hussain, J., Ali, T., Ali, S. I., Hafiz Syed, M. B., Lee, S., & Chung, T. (2021). Text classification in clinical practice guidelines using machine-learning assisted pattern-based approach. Applied Sciences, 11(8), 3296. doi:http://dx.doi.org/10.3390/app11083296 (Year: 2021).*

(Continued)

*Primary Examiner* — Emily Huynh
(74) *Attorney, Agent, or Firm* — Fish & Richardson P.C.

(57) ABSTRACT

Methods, systems, and apparatus, including computer programs encoded on computer storage media, for generating answers to medical questions using neural networks and other components. In one aspect, a method includes: receiving, from a user and by way of a user interface presented to the user on a display of a user device, a query for medical information; generating multiple responses to the query from the user by automatically retrieving and parsing data from a corpus of documents; and presenting, by way of the user interface and on the display of the user device: a first user interface element that presents a first response generated based only on clinical practice guideline documents, and a second user interface element that presents a second response generated based at least in part on documents that are not clinical practice guideline documents.

17 Claims, 8 Drawing Sheets

(56) References Cited

U.S. PATENT DOCUMENTS

| | | | | |
|---|---|---|---|---|
| 2014/0272885 | A1 | 9/2014 | Allen et al. | |
| 2018/0137249 | A1 | 5/2018 | Eggebraaten et al. | |
| 2018/0336183 | A1 | 11/2018 | Lee et al. | |
| 2020/0097814 | A1 | 3/2020 | Devesa | |
| 2020/0226164 | A1* | 7/2020 | Eifert | G06F 16/3334 |
| 2020/0303069 | A1* | 9/2020 | Mulligan | G06N 5/02 |
| 2021/0375404 | A1 | 12/2021 | Hu | |
| 2023/0394074 | A1 | 12/2023 | Panda et al. | |
| 2024/0126791 | A1 | 4/2024 | Yopadhyay et al. | |
| 2025/0029720 | A1 | 1/2025 | Sun et al. | |
| 2025/0087372 | A1* | 3/2025 | Bonageri | G06F 40/40 |

FOREIGN PATENT DOCUMENTS

| | | | | |
|---|---|---|---|---|
| JP | 2023-088036 | A | 6/2023 | |
| JP | 2023-553401 | A | 12/2023 | |
| JP | 2024-021725 | A | 2/2024 | |
| KR | 10-2021-0062809 | A | 6/2021 | |
| KR | 10-2642488 | B1 | 3/2024 | |
| WO | WO-2009083886 | A1 * | 7/2009 | G06F 19/3443 |
| WO | WO 2020034642 | A1 | 2/2020 | |

OTHER PUBLICATIONS

Bhandwaldar, "Biomedical question answering, " Thesis for the degree of Master of Science in Computer Science, UNC Charlotte, College of Computing and Informatics, 2017, 35 pages.

Aldhaleei et al., "Gucagon-Like Peptide-1 Receptor Agonists Associated Gastrointestinal Adverse Events: A Cross-Sectional Analysis of the National Institutes of Health All of Us Cohort," Pharmaceuticals, Feb. 2, 2024, 17(2):199, 11 pages.

Anil et al., "PaLM 2 Technical Report," CoRR, submitted on Sep. 13, 2023, arXiv:2305.10403v3, 93 pages.

Chen et al., "A Simple Framework for Contrastive Learning of Visual Representations," Presented at Proceedings of the 37th International Conference on Machine Learning, Vienna, Austria, Jul. 12-18, 2020; PMLR, Nov. 21, 2020, 119:1597-1607.

Devlin et al., "BERT: Pre-training of Deep Bidirectional Transformers for Language Understanding," CoRR, submitted on Oct. 11, 2018, arXiv:1810.04805v1, 14 pages.

Hadsell et al., "Dimensionality Reduction by Learning an Invariant Mapping," Presented at Proceedings of the 2006 IEEE Computer Society Conference on Computer Vision and Pattern Recognition, New York, NY, USA, Jun. 17-22, 2006; CVPR'06, Jun. 2006, pp. 1735-1742.

Jiang et al., "Mistral 7B," CoRR, submitted on Oct. 10, 2023, arXiv:2310.06825v1, 9 pages.

Long et al., "GLP-1 Agonists: A Review for Emergency Clinicians," The American Journal of Emergency Medicine, Jan. 12, 2024, 78:89-94.

Touvron et al., "Llama 2: Open Foundation and Fine-Tuned Chat Models," CoRR, submitted on Jul. 19, 2023, arXiv:2307.09288v2, 77 pages.

International Search Report and Written Opinion in International Appln. No. PCT/US2025/042666, mailed on Dec. 9, 2025, 13 pages.

Nguyen et al., "MedRedQA for Medical Consumer Question Answering: Dataset, Tasks, and Neural Baselines," Paper, Presented at the Proceedings of the 13th International Joint Conference on Natural Language Processing and the 3rd Conference on the Asia-Pacific Chapter of the Association for Computational Linguistics, Bali, Indonesia, Nov. 1-4, 2023, 1:629-648.

Office Action in Japanese Appln. No. 2025-024171, mailed on Oct. 28, 2025, 8 pages (with English translation).

Zhang et al., "Ranking Rule-Based Automatic Explanations for Machine Learning Predictions on Asthma Hospital Encounters in Patients With Asthma: Retrospective Cohort Study," JMIR Medical Informatics, Aug. 2021, 9(8):e28287, 22 pages.

* cited by examiner

Medical Database 150
Document Snippet N
Document Snippet 2
Document Snippet 1
Medical Question Answering System 100
Quality Assurance Engine 140
Embedding Model 134
Ranking Neural Network 136
Retrieval Engine 130
Generative Neural Network 120
Planner 110
Prompt 118
Answer 126
Medical Question 102

MEDICAL QUESTION ANSWERING SYSTEM

CROSS-REFERENCE TO RELATED APPLICATION

This application claims priority to U.S. Provisional Application No. 63/695,309, filed on Sep. 16, 2024. The disclosure of the prior application is considered part of and is incorporated by reference in the disclosure of this application.

BACKGROUND

This specification relates to question answering (QA). Question answering is a field in computer technology that attempts to automatically provide answers to questions input by humans, often in natural language format.

For example, in response to the input question "What is POTS?" a medical question answering system can use one or more machine learning models to process the input question and possibly other text data and output the answer that begins with "Postural orthostatic tachycardia syndrome (POTS) is a chronic disorder of the autonomic nervous system characterized by orthostatic intolerance and an excessive increase in heart rate upon standing."

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a medical question answering system implemented as computer programs on one or more computers in one or more locations that receives a medical question and uses neural networks and other components of the system to generate an answer to the medical question.

To generate the answer, the medical question answering system searches through a medical database that stores medical documents to obtain a set of document snippets from the medical database that are relevant to the medical question. The medical question answering system then incorporates the set of relevant document snippets into a prompt before processing the prompt using a generative neural network to generate the answer to the medical question.

According to an aspect, there is provided a method performed by one or more computers, the method comprising: obtaining question data representing a medical question; obtaining a plurality of document snippets from a medical database that stores medical documents, comprising performing a search in the medical database for document snippets relevant to the medical question using: (i) a respective embedding of each of the plurality of document snippets, and (ii) an embedding of the medical question; for each document snippet in the plurality of document snippets, determining a relevance score for the document snippet by using a ranking neural network based on the document snippet and the medical question; selecting, based at least in part on the relevance scores, a subset of the plurality of document snippets; generating a prompt that includes (i) the medical question and (ii) the subset of the plurality of document snippets; and generating an answer to the medical question based on processing the prompt using a generative neural network.

For each document snippet in the plurality of document snippets, determining the relevance score for the document snippet may comprise: processing, by the ranking neural network, an input that includes: (i) the medical question, and (ii) the document snippet, to generate a respective score for each of a plurality of different levels of relevance, wherein for each level of relevance, the respective score indicates a probability that a relevance between the medical question and the document snippet has the level of relevance; and determining the relevance score for the document snippet based on the respective score for each of the plurality of levels of relevance.

Determining the relevance score for the document snippet may comprise determining a linear combination of the respective scores.

Selecting, based at least in part on the relevance scores, the subset of the plurality of document snippets may comprise selecting, from the plurality of document snippets, and as an initial subset of the plurality of document snippets, highest scored document snippets that have highest relevance scores; for each of a plurality of aspects: assigning a respective weight to each document snippet in the initial subset of the plurality of document snippets with respect to the aspect; and selecting, from the document snippets in the initial subset of the plurality of document snippets, one or more document snippets based on the respective weight assigned to each document snippet.

The plurality of aspects may comprise one or more of: a recency of a medical document that includes the document snippet, quality of a provider of the medical document, or a relevancy between a user who submitted the medical question and an author of the medical document.

Selecting, based at least in part on the relevance scores, the subset of the plurality of document snippets may comprise: combining the one or more document snippets that have been selected for each of the plurality of aspects to generate a combined set of document snippets; and applying semantic filtering, deduplication, or both to the combined set of document snippets to generate the subset of the plurality of document snippets.

The prompt may also include one or both of: (iii) metadata associated with each document snippet in the subset of the plurality of document snippets, or (iv) predetermined instructions.

The answer to the medical question may comprise (i) a response generated by the generative neural network from processing the prompt, (ii) a citation listing of medical documents that include the subset of the plurality of document snippets, and (iii) data identifying a rationale for the medical documents being cited.

The reasons may comprise, for each document snippet in the subset of the plurality of document snippets, one or more of: a similarity explanation, an impact explanation, or a recency explanation.

Generating the answer to the medical question may comprise: processing at least the answer using a hallucination detection neural network to generate one or more hallucination detection outputs that indicate (i) whether any contradiction exists between (a) the response generated by the generative neural network from processing the prompt and (b) the subset of the plurality of document snippets, (ii)

whether at least one document snippet in the subset of the plurality of document snippets supports the response generated by the generative neural network from processing the prompt, or both (i) and (ii).

The method may further comprise: determining that a contradiction exists; and in response, modifying the response generated by the generative neural network to generate a modified response.

Obtaining question data representing a medical question may comprise: receiving an initial user input; and pre-processing the initial user input to generate the medical question, wherein the medical question (i) is in a predetermined natural language, (ii) has a question format, (iii) expands any acronyms or abbreviations in the initial input, and (iv) replaces any brand names in the initial input with generic names.

The ranking neural network may be trained based on optimizing a supervised learning objective function on a ranking training dataset that includes a plurality of ranking training pairs, wherein each ranking training pair (i) includes a medical question and a document snippet and (ii) is associated with a ground truth score for each of the plurality of different levels of relevance.

Obtaining the plurality of document snippets may comprise: for each document snippet, determining a distance between (i) a respective embedding of the document snippet and (ii) the embedding of the medical question; and selecting, as the plurality of document snippets, document snippets based on the distances.

For each of the plurality of document snippets, the respective embedding may be generated by an embedding model from processing the document snippet.

The embedding model may be trained based on optimizing a contrastive learning objective function on an embedding training dataset that includes a plurality of embedding training pairs, wherein each embedding training pair includes a medical question and a document snippet.

For each embedding training pair, the document snippet may be extracted from a source medical document, and the medical question may be generated by a language model neural network based on processing the document snippet.

Two or more of the plurality of embedding training pairs may include a same document snippet, and the contrastive learning objective function may include a term that punishes the embedding model for generating respective embeddings of medical questions included in the two or more of the plurality of embedding training pairs that are different from each other.

According to another aspect, there is provided a method performed by one or more computers, the method comprising: receiving, from a user and by way of a user interface presented to the user on a display of a user device, a query for medical information; generating a response to the query from the user by automatically retrieving and parsing data from a corpus of documents, comprising: determining, based on an automated search of the corpus of documents, that one or more clinical practice guideline documents from the corpus of document include information that is responsive to the query; in response to determining that one or more clinical practice guideline documents include information that is responsive to the query, generating a first response to the query based only on clinical practice guideline documents; and generating a second response to the query based at least in part on one or more other documents that are not clinical practice guideline documents; and presenting, by way of the user interface and on the display of the user device: a first user interface element that presents the first response generated based only on clinical practice guideline documents, wherein the first user interface element visually highlights that the first response is derived only from clinical practice guideline documents and identifies one or more clinical practice guideline document that were processed to generate the first response; and a second user interface element that presents the second response generated based at least in part on documents that are not clinical practice guideline documents.

The first user interface element may be presented on top of and temporally before the second user interface element within the user interface.

The first user interface element may comprise a walled garden environment presented within the user interface, and the first response generated may be based only on the clinical practice guideline documents is presented within the walled garden environment.

The first user interface element may comprise a header that indicates the first response is generated based only on clinical practice guideline documents.

Generating the first response to the query based only on clinical practice guideline documents may comprise making a first call to a generative neural network, and wherein generating the second response to the query based at least in part on one or more other documents that are not clinical practice guideline documents may comprise making a second call to the generative neural network after the generative neural network has generated the first response in response to the first call.

Generating the first response to the query based only on clinical practice guideline documents may comprise: processing, by the generative neural network, a first prompt that includes (i) the query for medical information and (ii) the clinical practice guideline documents, to generate the first response.

Generating the second response to the query based at least in part on one or more other documents that are not clinical practice guideline documents may comprise: processing, by the generative neural network, a second prompt that includes (i) the query for medical information, (ii) the one or more other documents, and (iii) the first response generated by the generative neural network, to generate the second response.

According to another aspect, there is provided one or more computer-readable storage media encoded with instructions that, when executed by one or more computers, cause the one or more computers to perform the operations of the above method aspects.

According to a further aspect, there is provided a system comprising one or more computers and one or more storage devices storing instructions that when executed by one or more computers cause the one or more computers to perform the respective operations of the above method aspects.

The subject matter described in this specification can be implemented in particular embodiments so as to realize one or more of the following advantages.

Vast amounts of expert knowledge are stored in databases, e.g., in the form of medical documents describing clinical trials, academic journal articles describing scientific and medical research, and the like. By performing the two-stage process described in this specification to retrieve relevant and up-to-date information form a database in a computationally effective and accurate manner, and then causing a generative neural network to generate answers in response to questions by leveraging the retrieved information (instead of merely stale information that was available at the time of the training of the generative neural network), the medical question answering system can generate answers that are more accurate and timely.

Compared to existing question answering systems, the medical question answering system described in the specification is capable of generating answers that have a much greater likelihood of being scientifically reliable and factually accurate, e.g., answers that are more likely to be grounded in external, verified medical databases or other knowledge repositories, such as published papers, medical guidelines, or established reference materials, which are continually kept up-to-date, while having a much lower likelihood of having any hallucination included as part of the answers.

The medical question answering system is particularly advantageous in a wide range of real-world scenarios that involve scientifically grounded clinical decision making. For example, the medical question answering system can generate answers that help clinicians in an active setting (such as a treatment room) quickly and efficiently answer free-form questions that are relevant for the past and future treatment of a patient, such as dosages, contraindications, side-effects, drug interactions, condition symptoms, possible second- and third-line treatments, safety aspects, etc.

From another point of view, the medical question answering system functions as an interface between a user and a large corpus of medical documents that is otherwise too large to be searched in response to a question that the user might pose with respect to the medical documents. This interface makes it practically possible for the user to leverage the information contained in the prohibitively large corpus of medical documents to retrieve a set of reliable information, and in particular information which is verifiably correct.

Various techniques described in this specification enable the medical question answering system to achieve these advantages with reduced consumption of computing resources. For one, by using the two-stage search process that includes a relatively less computationally intensive first stage followed by a relatively more computationally intensive second stage described in this specification, the medical question answering system can generate the answers with reduced consumption of computing resources such as memory and computing power. In other words, the two-stage search process described in this specification makes it computationally feasible to search a massive corpus of documents.

In particular, the first stage in the two-stage search process involves performing a rough filtering based on embeddings, and is less computationally intensive because it involves computing an embedding of the medical question and then measuring similarities between the medical question embedding and multiple pre-computed medical snippet embeddings that can be reused for different medical question embeddings. Meanwhile, the second stage in the two-stage search process involves performing a fine-grained ranking using a ranking neural network, and is more computationally intensive because it requires processing each of multiple document snippets using the ranking neural network.

For another, many existing question answering systems often generate answers that include hallucination. In contrast, the described techniques that relate to hallucination detection improves the possibility that answers generated by the medical question answering system are scientifically reliable and factually accurate, and that are free from hallucination, by performing hallucination detection at various levels, e.g., at sentence level, paragraph level, and so on, of the content included in the generated answer based on the content of the medical documents stored in the medical database. The medical question answering system described in this specification is thus suitable for deployment at production environments such as within an educational or medical organization in which false or misleading information may result in serious consequences.

For another, the described techniques that relate to contrastive training improves the computing resource efficiency in training an embedding model neural network that is used to facilitate the two-stage search process. Unlike in many conventional contrastive training setups where an equal or about equal number of medical question embeddings and document snippet embeddings would need to be generated during training, the specification describes a training setup where the embedding model neural network is configured to generate more medical question embeddings than document snippet embeddings. Since a medical question may be shorter in length than a document snippet, generating an embedding of the medical question can save computational cost compared to generating an embedding of the document snippet because a smaller amount of data needs to be processed by the embedding model neural network.

The savings in computational cost can be significant when embeddings of only a relatively small number of document snippets, relative to the number of medical questions, need to be generated, e.g., generate one document snippet embedding for every 3, 5, or 10 medical question embeddings, rather than generating a document snippet embedding for every single medical question embedding.

For another, the described techniques that relate the improved user interface can help users to more clearly distinguish between answers that are generated based solely on clinical practice guideline documents and answers that are not, and to gain insights for improving review efficiency. The described techniques also represent an improvement to user interface technology. By generating an answer based on the clinical practice guidelines and presenting the answer to the user with an appropriate visual indication, and then, after having presented the answer to the user, proceeding to generate another answer based on the other medical documents for presentation to the user at a later time with a different visual indication, the described techniques reduce latency in providing and presenting content that satisfies the informational needs of the user, and minimize potential confusion with respect to different answers to the same medical question that are generated based on different source documents.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

SUMMARY

Figure 1:
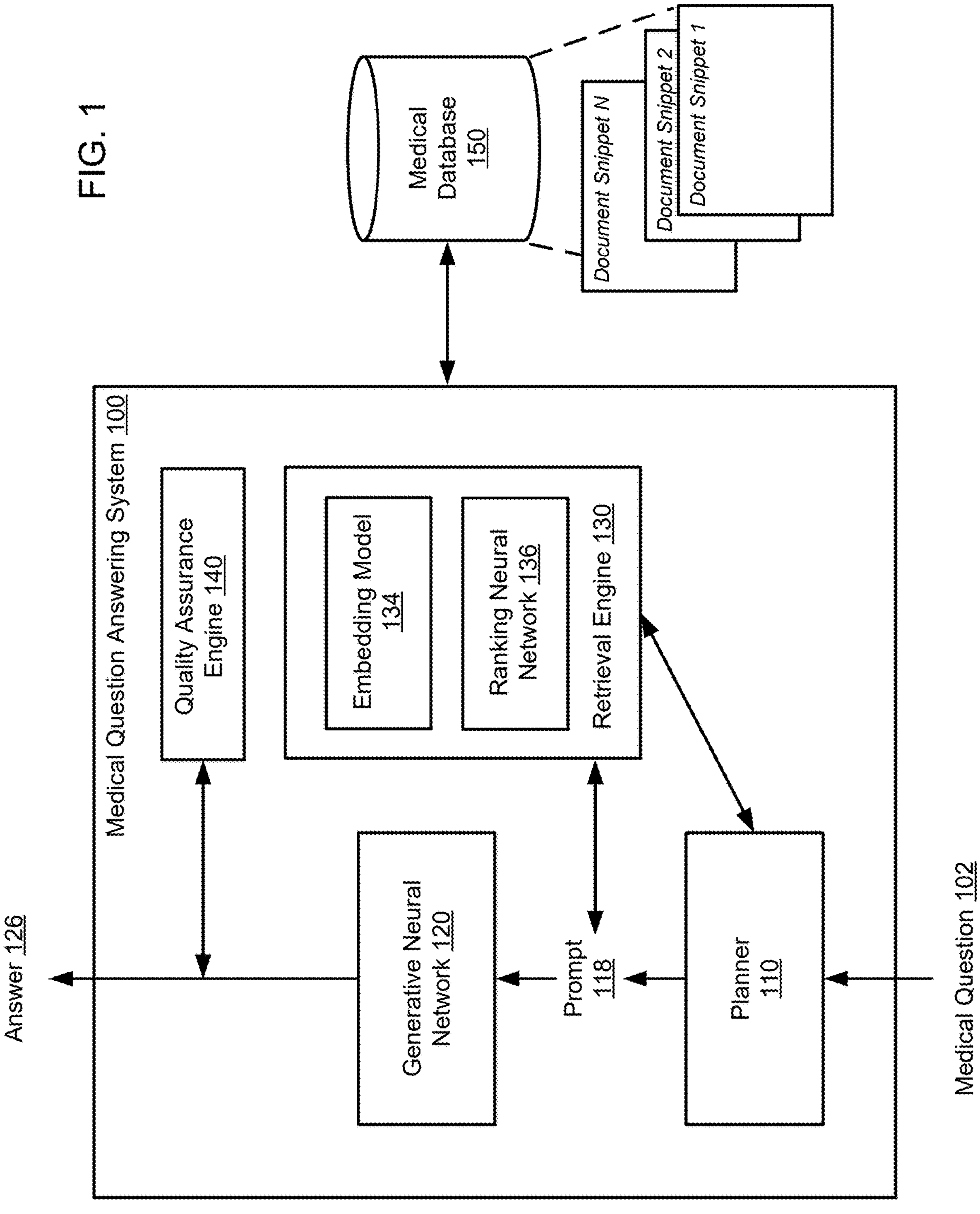
FIG. 1 is a diagram of an example medical question answering system.

FIG. 1 shows an example medical question answering system 100. The medical question answering system 100 is an example of a system implemented as computer programs on one or more computers in one or more locations that receives a medical question 102 and uses neural networks and other components of the system to generate an answer 126 to the medical question.

The medical question answering system 100 can obtain data representing the medical question 102 in any of a variety of ways. In some cases, the data representing the medical question 102 is also called "question data." In some cases, the medical question 102 is also called a "query," a "prompt," or a "question."

In some cases, the question data includes text data, and the medical question answering system 100 receives the question data as a text query from a user submitted through a user interface of a user device. For example, the medical question 102 may be entered by the user by typing using a data input device, e.g., a keyboard, a touch screen, a wearable device (such as a smartwatch), a smart home device (such as a smart speaker), or another handheld or desktop input device.

In some other cases, the question data includes audio data, and the medical question answering system 100 receives the question data as a natural language speech query from the user and converts the speech into the medical question 102 by applying a speech recognition engine to the speech. For example, the medical question 102 may be received in the form of a sound (speech) signal, captured by a microphone of the user computer, which is converted by a speech recognition engine, i.e., a speech-to-text converter to form the medical question 102.

The medical question answering system 100 has access to a medical database 150. The medical database 150 can be any database that stores a corpus of medical documents in the form of document snippets. That is, the medical database 150 stores a plurality of document snippets that are included in the corpus of medical documents.

A medical document is an electronic document that includes medical-related content. Examples of medical documents include webpages, word processing documents, spreadsheet documents, presentation documents, portable document format (PDF) documents and so on.

In practice, the medical database 150 can include vast numbers of medical documents, e.g., at least 100,000 medical documents, or at least 1,000,000 medical documents, or at least 10,000,000 medical documents. Moreover, the medical database 150 can dynamically change over time, e.g., as new medical documents are added, or as medical documents are removed (e.g., as new clinical practice guidelines replace old ones, or as published papers are retracted, etc.).

The corpus of medical documents may for example include webpages and other electronic documents accessible through the Internet. Additionally or alternatively, the corpus of medical documents may, for example, be part of a proprietary medical database, e.g., of a scientific content publisher (e.g., a physical science content publisher, a life science content publisher, a health science content publisher, or a social science content publisher), a technical content publisher, a medical content publisher, or other organization. Optionally, the corpus of medical documents may include clinical practice guideline documents.

A clinical practice guideline document is a document that include information about clinical practice guidelines. Clinical practice guidelines are statements that include recommendations, intended to optimize patient care, that are informed by a systematic review of evidence and an assessment of the benefits and harms of alternative care options. Clinical practice guidelines can be used to, for example: inform individual clinical decision-making, provide best practice recommendations for the treatment and care of people by health professionals, develop standards to guide and assess the clinical practice of individual health professionals and healthcare organizations, help educate and train health professionals, and help patients make informed decisions.

A "document snippet" includes at least some content of a full electronic document. In some implementations, the lengths of the plurality of document snippets can vary. For example, each document snippet can correspond to a paragraph, a page, or a chapter of an electronic document.

In some implementations, the plurality of document snippets can each have about equal length. For example, each document snippet can have about 100 words, 300 words, or 500 words, or the like. As another example, each document snippet can have about 100 sub-words, 300 sub-words, or 500 sub-words, or the like. A sub-word is generally an incomplete word, although there may also be sub-words corresponding to complete words in a vocabulary. For example, the word "certainly" may include a sub-word "certain" and a sub-word "ly".

In some implementations, the medical question answering system 100 or another database system can generate the plurality of document snippets by applying a sliding window technique to each medical document in corpus of medical documents to extract each possible sequence of a predetermined fixed length of words or sub-words from the medical document. The extracted sequences of words or sub-words can then be stored as document snippets in the medical database 150.

Figure 2:
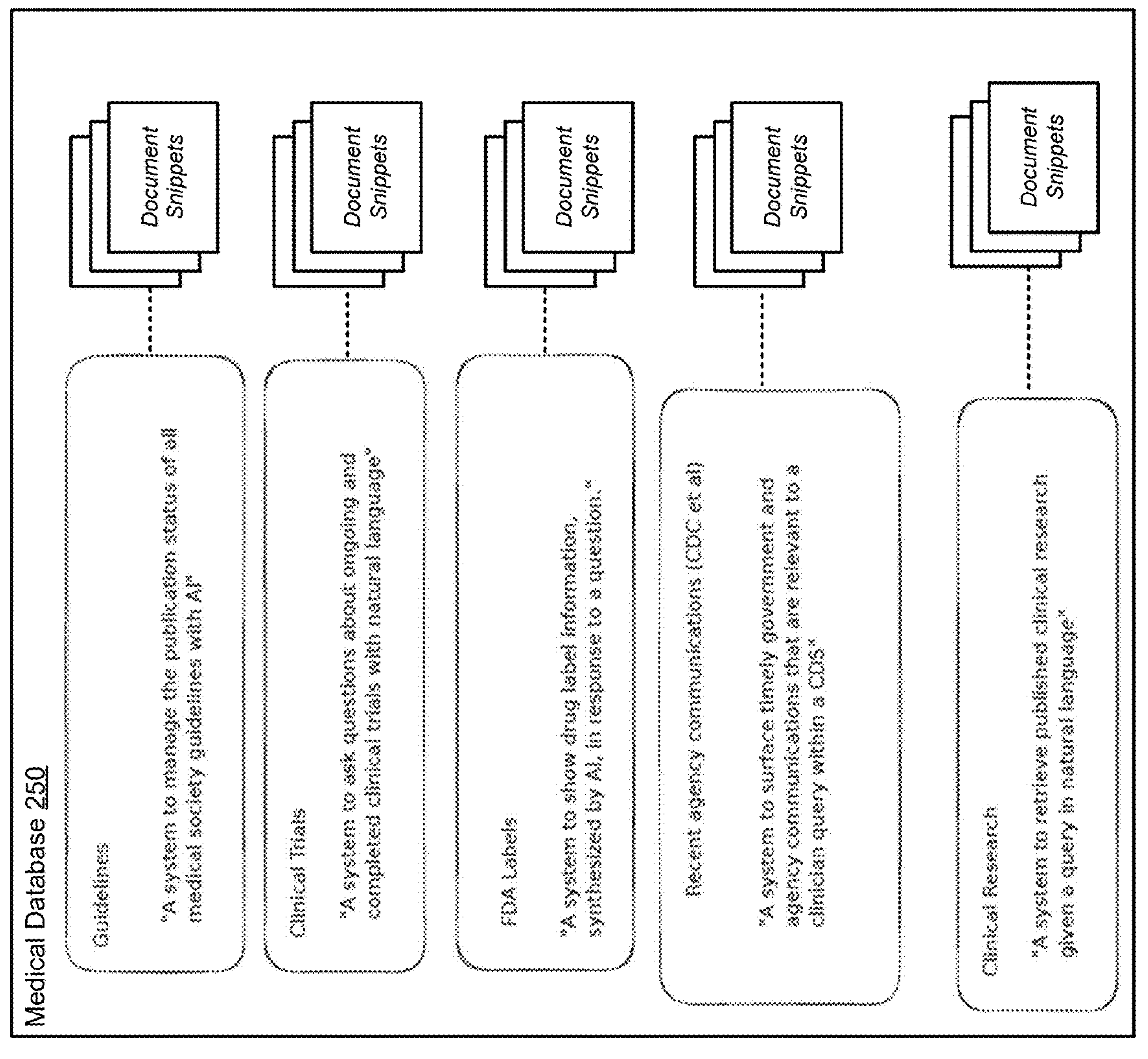
FIG. 2 is an illustration of an example of a medical database.

FIG. 2 is an illustration of an example of the medical database 150.

As illustrated, the medical database 150 can store document snippets included in a plurality of guideline documents, e.g., clinical practice guideline documents or regulatory guideline documents, that include information about guidelines, standards, regulations, etc. The medical database 150 can store document snippets included in a plurality of clinical trial documents that include clinical information about different entities including disease entity, drug name, line of therapy, etc. The medical database 150 can store document snippets included in medical label documents, e.g., drug label documents that include labels for drug products that have been approved by the Food and Drug Administration (FDA) or another government agency. The medical database 150 can store document snippets included in a plurality of agency communication documents, e.g., copies of communications issued by the Centers for Disease Control and Prevention (CDC) or another government agency. The medical database 150 can also store document snippets included in a plurality of clinical research documents, e.g., scientific or clinical research publications.

Upon receiving the medical question 102, the medical question answering system 100 uses a planner 110 to orchestrate the operations performed by the neural networks and the other components of the system when generating the answer 126 in response to the medical question 102.

Figure 3:
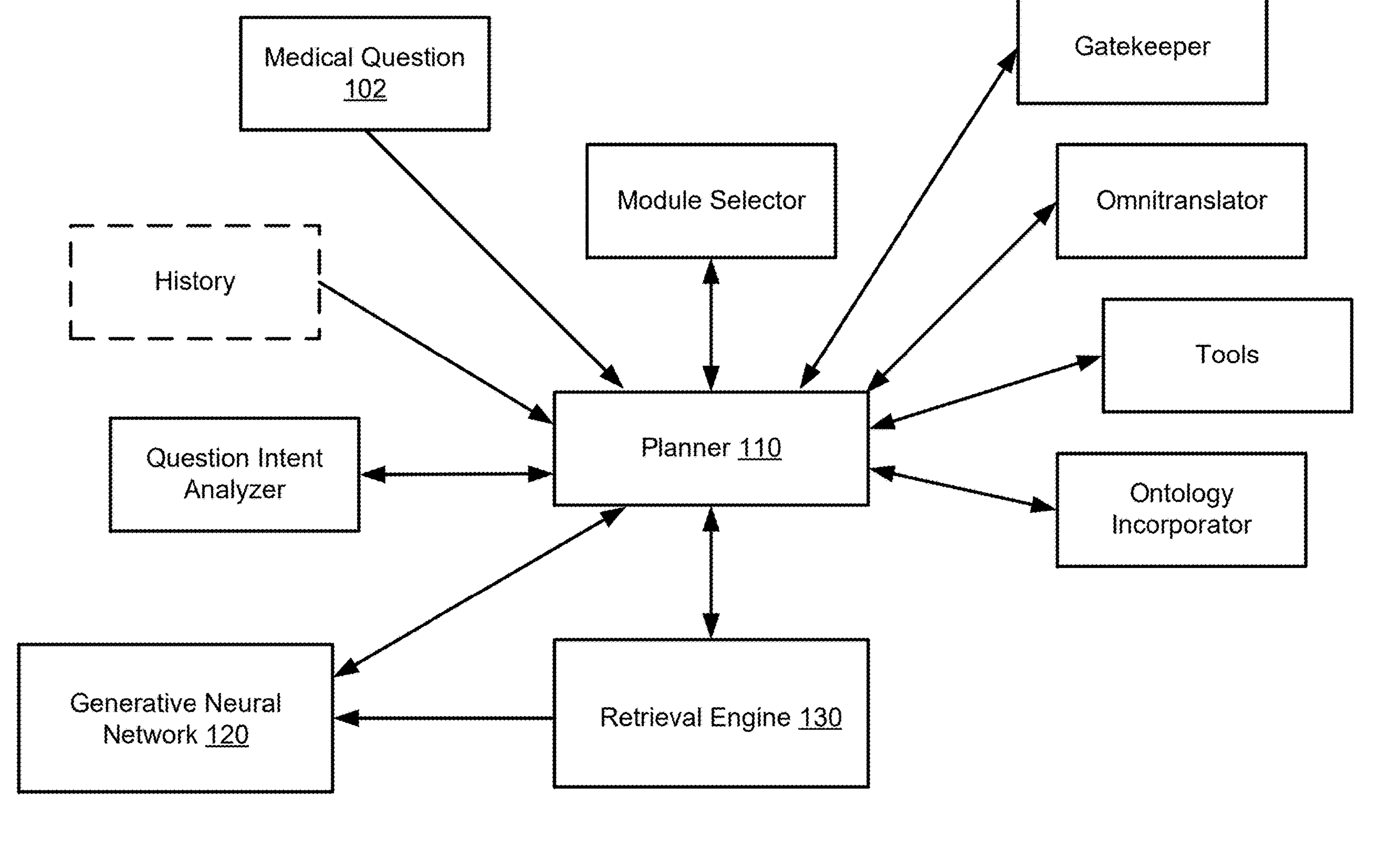
FIG. 3 is an illustration of example operations performed by a planner.

FIG. 3 is an illustration of example operations performed by the planner 110.

In some implementations, the medical question answering system 100 includes or has access to multiple candidate generative neural networks, and the planner 110 can act as a module selector. The module selector can select one of the multiple candidate generative neural networks as the generative neural network 120 to generate the answer 126 in response to the medical question 102. The module selector can use any suitable approach to select between the multiple candidate generative neural networks.

For example, the module selector can make this selection based on the medical question, e.g., based on a length, a receipt time, or another aspect of the medical question. As another example, the module selector can make this selection based on the availability or utilization of the multiple candidate generative neural networks.

As another example, the module selector can make this selection based on the availability of the computing resources (e.g., processing power, memory and other storage, bandwidth, etc.) of the medical question answering system 100—for example by selecting a candidate generative neural network that has a larger memory footprint and a higher processing power consumption requirement when a greater amount of computing resources is available, while selecting a candidate generative neural network that has a smaller memory footprint and a lower processing power consumption requirement when only a reduced amount of computing resources is available.

Typically, a candidate generative neural network that has more parameters or a more complex architecture, e.g., that includes more layers, has a larger memory footprint and a higher processing power consumption then another candidate generative neural network that has fewer model parameters or a less complex architecture, e.g., that includes fewer layers.

The availability of computing resources can vary based on the total number of medical questions that have been received at the same time, the geographic regions from which the medical questions that have been received, or other factors. As some particular examples, the module selector can select a lightweight candidate generative neural network when more than a threshold number of medical questions received have been received during a particular time window, or select a lightweight generative neural network for medical questions received from users located in geographical regions that are more than a threshold distance away from the medical question answering system 100.

In some implementations, the planner 110 can act as a gatekeeper. The gatekeeper ensures that the medical question answering system 100 do not waste computing resources in responding to irrelevant queries that the system might receive from various users.

To that end, the gatekeeper can parse question data submitted to the system 100 to determine whether the question data includes a medical question, i.e., whether a question submitted by a user is about a medical topic. For example, the gatekeeper can use the generative neural network 120 or some other text classification machine learning model to process the question data to generate a classification output that specifies whether a question represented by the question data is a medical question or not.

In cases where gatekeeper determines that the question data does not include a medical question, the gatekeeper could reject the question—for example it could provide to the user predetermined response without using other components of the system 100 to further process the question data. For example, the gatekeeper can reject the question "What is 2+2?" by way of providing a predetermined response "The question is outside the scope of the medical question answering system."

The gatekeeper can also convert the medical question submitted by the user, which may be in an initial form (such as a free-text form), into a refined form that is more suitable for further processing by the other components of the system 100.

In some implementations, the gatekeeper can reduce erroneous content such as typo or grammatical errors from the medical question in the initial form. In some implementations, the gatekeeper can expand the acronyms, abbreviations, and other shorthand included in the medical question in the initial form. In some implementations, the gatekeeper can replace certain words or phrases included in the medical question in the initial form with more precise medical terminology. For example, the gatekeeper can convert a medical question in the initial form "How does keto diet affect diabetes?" into a medical question in the refined form "How does the ketogenic diet affect type 2 diabetes?"

In some implementations, in response to receiving the medical question in the initial form, the gatekeeper can pre-process the medical question in the initial form to generate the medical question in a predetermined refined form. Specifically, the medical question that is in the predetermined refined form (i) is in a predetermined natural language, (ii) has a question format, (iii) expands any acronyms or abbreviations that might be included in the medical question in the initial form, and (iv) replaces any brand names that might be included in the medical question in the initial form with generic names.

For example, the gatekeeper can do this by converting the medical question from the initial form into the predetermined refined form based on using a predetermined conversion template. As another example, the gatekeeper can do this by using the generative neural network 120 or another neural network—for example by using the generative neural network 120 to process an input that includes the medical question in the initial form and data that defines the predetermined refined form to generate an output that includes the medical question in the predetermined refined form.

In some implementations, the planner 110 can act as a translator, e.g., an omni translator that translates text in different source natural languages into text in a common target natural language. For example, the translator can translate a medical question that is in the form of a sequence of words in a source natural language into a medical question that is in the form of a sequence of words in a target natural language. In this example, the answer 126 can be in the form of another sequence of words that is likewise in the source natural language.

In some implementations, the medical question answering system 100 includes or has access to multiple external tools, and the planner 110 can act as a tool selector. The multiple external tools are separate from the generative neural network 120 and, in some implementations, separate, e.g., remote, from the system 100.

An external tool can generally be any software function that is queryable by the medical question answering system 100, e.g., through application programming interface (API) calls, to provide data in response to a query. Examples of these external tools include a calculator tool (such as a drug dosage calculator tool) and a calendar tool, to name just a few.

The tool selector can select one or more of the multiple external tools to generate responses that can be incorporated into the answer 126 to be generated by the generative neural network 120 in response to the medical question 102. Like the module selector, the tool selector can use any suitable approach to select between the multiple external tools, e.g., based on the medical question, the availability or utilization of the multiple external tools, and so on.

In some implementations, the planner 110 can act as an ontology incorporator. The ontology incorporator maps certain words or phrases in the medical question to nodes in an ontology graph, which is used to augment a retrieval process to be performed by a retrieval engine 130 by providing the retrieval engine 130 with access to synonymous, hyponymous, or other terms. The ontology graph includes a set of nodes which are connected by edges. The nodes of the ontology graph can represent medical concepts such as the name of drugs or medical conditions. The edges of the ontology graph can represent relationships between drugs, such as "is a precursor for", "is equivalent to", "is a version of," or other relationships.

In some implementations, the planner 110 can act as a question intent analyzer that can augment the retrieval process to be performed by the retrieval engine 130. The question intent analyzer can use the generative neural network 120 or some other text classification model to determine an intent of the medical question, and subsequently determine which group(s) of document snippets included in the medical database 150 should be searched based on the intent.

For example, the question intent analyzer can determine that document snippets included in clinical trial documents should be searched in response to determining that an intent of the medical question relates to clinical trial purposes. As another example, the question intent analyzer can determine that document snippets included in academic journal articles should be searched in response to determining that an intent of the medical question relates to academic research purposes.

The question intent analyzer can thus reduce the consumption of computational resources by the medical question answering system 100 because exhaustively searching through the entire medical database 150 can be avoided. In some implementations, the question intent analyzer can be implemented as a classification model, e.g., a classification neural network, that is configured to process the medical question to generate a classification output that includes a score distribution over a set of possible categories of document. Correspondingly, only documents in some of the categories in the set that have scores that satisfy a threshold will need to be searched. For example, the group(s) of document snippets that need to be searched in response to the medical question based on the classification output may be less than 50%, or less than 10%, or less than 5% of the entire medical database.

To generate the answer 126 in response to the medical question 102, the medical question answering system 100 uses the retrieval engine 130 to search through the medical database 150 to obtain, based on the medical question 102, a smaller subset of document snippets from the medical database 150 that are relevant to the medical question 102.

The medical question answering system 100 then incorporates the smaller subset of document snippets into a prompt 118 before processing the prompt 118 using the generative neural network 120 to generate the answer 126 to the medical question 102.

For example, the medical question answering system 110 can generate a prompt 118 that includes the medical question and the smaller subset of the document snippets, and then cause the generative neural network 120 to generate the answer 126 to the medical question 102 based on processing the prompt 118.

Optionally, the prompt 118 also includes a predetermined set of system instructions. For example, the predetermined set of system instructions can be represented by text in some natural language, e.g., text that describes what may or may not be included in the answer 126. Optionally, the prompt 118 also includes the results received from one or more external tools, e.g., an amount of dosage calculated by a drug dosage calculator tool. Optionally, the prompt 118 also includes one or more historic medical questions received by the system 100 and one or more answers generated by the system 100 in response to the historic medical questions. Optionally, the prompt 118 also includes metadata associated with each document snippet in the subset of the plurality of document snippets. For example, the metadata can include the publication dates of the medical documents from which the document snippets in the subset are obtained.

In this way, the answer 126 will incorporate information contained in the smaller subset of document snippets, including up-to-date information that was not available during the training of the generative neural network and/or proprietary information that was not publicly available and thus might be excluded from the training data used to train the generative neural network, thus improving the quality, e.g., helpfulness, factual accuracy, comprehensiveness, up-to-dateness, or some combination thereof, of the answer 126 in view of the medical question 102.

The generative neural network 120 can be or include a (large) language model that has been configured through training to enable it to receive an input sequence made up of tokens selected from a vocabulary and auto-regressively generates an output sequence made up of tokens from the vocabulary. For example, the input sequence can represent the prompt 118, while the output sequence can represent the answer 126 to the medical question 102.

The vocabulary of tokens can include any of a variety of tokens that represent text symbols or other symbols. For example, the vocabulary of tokens can include one or more of characters, sub-words, words, punctuation marks, numbers, or other symbols that appear in a corpus of natural language text.

For example, the language model can have any of a variety of Transformer-based neural network architectures, e.g., encoder-only Transformer architectures, encoder-decoder Transformer architectures, decoder-only Transformer architectures, other attention-based architectures, and so on. As another example, the language model can have any of a variety of recurrent neural network architectures.

Example implementations of such a language model are described in more detail in Anil, Rohan, et al. "Palm 2 technical report." arXiv preprint arXiv:2305.10403; and Touvron, Hugo, et al. "Llama 2: Open foundation and fine-tuned chat models." arXiv preprint arXiv:2307.09288 (2023), Jiang, Albert Q., et al. "Mistral 7B." arXiv preprint arXiv:2310.06825 (2023), but others may also be used.

More specifically, the auto-regressively generated output sequence is created by generating each particular token in the output sequence conditioned on a current input sequence that includes any tokens that precede the particular text token in the output sequence, i.e., the tokens that have already been generated for any previous positions in the output sequence that precede the particular position of the particular token, and the tokens included in the prompt 118.

To generate a particular token at a particular position within an output sequence, the generative neural network 120 can process the current input sequence to generate a score distribution, e.g., a probability distribution, that assigns a respective score, e.g., a respective probability, to each token in the vocabulary of tokens. The generative neural network 120 can then select, as the particular token, a token from the vocabulary using the score distribution. For example, the neural network of the generative neural network 120 can greedily select the highest-scoring token or can sample, e.g., using nucleus sampling or another sampling technique, a token from the distribution.

In many scenarios, the medical database 150 can be a large database that stores a very large number of, e.g., ten million, a hundred million, a billion, or more, medical documents, and therefore even a larger number of document snippets. This very large number of document snippets that need to be searched in these scenarios presents challenges to a system configured to computationally effectively search through and accurately select from the medical database a smaller number of document snippets that are relevant to the medical question.

To address these challenges, as will be discussed further below with reference to FIGS. 4-5, some implementations of the medical question answering system 150 use the retrieval engine 130 to retrieve the smaller subset of document snippets by performing the search using a two-stage process: an initial retrieval step that retrieves a plurality of document snippets from the document snippets stored in the medical database 150, followed by a re-ranking step that selects a proper subset of document snippets from the plurality of document snippets that have been retrieved from the medical database 150 in the initial retrieval step.

A "proper subset" of the plurality of document snippets contains at least one document snippet, but fewer than all of the plurality of document snippets that have been retrieved in the initial retrieval step from the document snippets stored in the medical database 150.

The retrieval engine 130 performs the two-stage process using multiple neural networks. The initial retrieval step is performed using an embedding model neural network 134. Then, the re-ranking step is performed using a ranking neural network 136.

The embedding model neural network 134 (or "embedding model 134" for short) can have any appropriate neural network architecture which enables the embedding model 134 to process a medical question to generate an embedding of the medical question (a "medical question embedding"), or process a document snippet to generate an embedding of the document (a "document snippet embedding").

An embedding is an ordered collection of numeric values in an embedding space. For example, an embedding can include one or more vectors of floating point or other numeric values that has a fixed dimensionality. The medical question embedding and the document snippet embeddings generally have the same dimensionality, i.e., the medical question embedding and each document snippet embedding have the same number of numeric values.

For example, the embedding model 134 can include any appropriate types of neural networks layers (e.g., fully-connected layers, embedding layers, attention layers, etc.) in any appropriate number (e.g., 5 layers, 10 layers, or 20 layers) and connected in any appropriate configuration (e.g., as a linear sequence of layers).

In some implementations, the embedding model 134 can be initialized using a base language model that has been pre-trained using unsupervised learning. That is, the embedding model 134 can start with the same architecture and weights as (at least some part of) the base language model which has been trained on a corpus of text to perform one or more language modeling tasks that do not require labeled training examples. For example, the embedding model 134 can be initialized using the base language model described in Devlin, Jacob. "Bert: Pre-training of deep bidirectional transformers for language understanding." arXiv preprint arXiv:1810.04805 (2018).

After the initialization, the embedding model 134 can then be fine-tuned on a custom embedding training dataset to learn fine-tuned weights based on optimizing a fine-tuning objective function. The custom embedding training dataset includes a plurality of embedding training pairs. Each embedding training pair includes a medical question and a document snippet.

By construction, each embedding training pair can be a positive embedding training pair, such that the document snippet includes information that is relevant to answering the medical question, or can alternatively be a negative embedding training pair, such that the document snippet includes information that is irrelevant to answering the medical question.

Such a custom embedding training dataset can be automatically generated by the system 100 or another training system based on medical documents that are available, e.g., the medical documents stored in the medical database 150. In some implementations, for each embedding training pair, the document snippet can be one of the document snippets extracted from a source medical document, and the medical question can be generated by a language model neural network based on processing the document snippet. For example, the language model neural network can be used to process a prompt that includes: (i) the document snippet, and (ii) an instruction that includes text in some natural language, to generate a medical question that can be (or cannot be) answered at least in part by the document snippet.

In some implementations, multiple medical questions can be generated by using the language model neural network based on processing the same medical document, or even for the same document snippet. Thus, two or more of the plurality of embedding training pairs can include a same document snippet.

Since a medical question may be shorter in length than a document snippet, generating an embedding of the medical question can save computational cost compared to generating an embedding of the document snippet because a smaller amount of data needs to be processed by the embedding model 134. The savings in computational cost during training can be significant when embeddings of only a relatively small number of document snippets, relative to the number of medical questions, need to be generated, e.g., in a training setup where the embedding model 134 is configured to generate embeddings of multiple medical questions for every document snippet.

In implementations where multiple medical questions are generated for a document snippet, they can be generated in a way such that one of the multiple medical questions can be answered by the document snippet, while others of the multiple medical questions cannot. After having generated the multiple medical questions, multiple embedding training pairs—including positive embedding training pair and one or more negative embedding training pairs—can then be generated.

That is, a positive embedding training pair that includes the document snippet and the medical question that can be answered by the document snippet can be generated. Also, one or more negative embedding training pairs that each include the document snippet and a medical question that cannot be answered by the document snippet can be generated.

In these implementations, the fine-tuning objective function can be a contrastive learning objective function. The contrastive learning objective function includes a term that encourages the embedding model 134 to generate similar embeddings (according to some similarity measure) for the medical question and the document snippet that are included in each positive embedding training pair.

For example, the similarity measure can be a distance measure in an embedding space that is determined based on one of: a Euclidean distance, a Manhattan distance, or another distance measure, and term (when used to compute gradient-based updates to the parameters of the embedding model 134) can push the embeddings generated by the embedding model 134 for the medical question and the document snippet that are included in each positive embedding training pair closer together in the embedding space, i.e., reduces the distance between the medical question embedding and the document snippet embedding generated by the embedding model 134.

The contrastive learning objective function also includes another term that encourages the embedding model 134 to generate different embeddings (according to some similarity measure) for the medical question and the document snippet that are included in each negative embedding training pair. Put another way, for each negative embedding training pair, the other term penalizes the embedding model 134 for generating similar embeddings (according to some similarity measure) for the medical question and the document snippet that are included in the negative embedding training pair.

For example, the similarity measure can similarly be a distance measure in an embedding space, and the other term (when used to compute gradient-based updates to the parameters of the embedding model 134) can push the embeddings generated by the embedding model 134 for the medical question and the document snippet that are included in each negative embedding training pair apart in the embedding space, i.e., increases the distance between the medical question embedding and the document snippet embedding generated by the embedding model 134.

Examples of contrastive loss functions that the system can use for training the embedding model are described in: Chen, T., Kornblith, S., Norouzi, M., & Hinton, G. (2020). "A Simple Framework for Contrastive Learning of Visual Representations." In Proceedings of the 37th International Conference on Machine Learning (ICML); and Hadsell, R., Chopra, S., & LeCun, Y. (2006). "Dimensionality Reduction by Learning an Invariant Mapping." In Proceedings of the 2006 IEEE Computer Society Conference on Computer Vision and Pattern Recognition (CVPR).

In general, for some or all of the training pairs (i.e., that each include a respective medical question and document snippet), the medical question has a shorter length than the document snippet. For instance, the medical question can have a length that is <50%, or <10%, or <5% the length of the document snippet. In particular, medical questions can include a sentence, or a paragraph, a series of paragraphs; while document snippets can include some or all of entire documents that include many paragraphs of text. Thus processing a medical question using the embedding model to generate an embedding of the medical question may consume substantially less computational resources (e.g., memory and computing power) than processing a document snippet using the embedding model to generate an embedding of the document snippet.

The system can leverage the asymmetry in the lengths of medical questions as compared to document snippets in order to increase the efficiency of training the embedding model. In particular, at each training iteration, the system can, for each of one or more document snippets, identify one "positive" medical question for which the document snippet is responsive to the medical question, and N "negative" medical questions for which the document snippet is not responsive to the medical question, where N is any positive integer value, e.g., N=3, or N=5, or N=10, or N=100. The system then processes the document snippet, the positive medical question, and the N medical questions using the embedding model (and in accordance with current values of the set of embedding model parameters) to generate corresponding embeddings. The system then measures distances between the embeddings and backpropagates gradients of a contrastive loss objective function that is dependent upon those embeddings through the embedding model (e.g., the embedding neural network). In this manner, the system can drastically reduce consumption of computational resources as compared to an implementation where, for each of one or more medical questions, the system identifies one "positive" document snippet that is responsive to the medical question and N "negative" document snippets that are not responsive to the medical question.

The ranking neural network 136 is configured to, for a document snippet, process an input that includes: (i) the medical question and (ii) the document snippet to generate an output that includes a score for each of a plurality of different levels of relevance. For each level of relevance, the score can be a probability score (e.g., between 0 and 1, inclusive on both ends) that indicates a probability that a relevance between the medical question and the document snippet has the level of relevance.

The ranking neural network 136 can have any appropriate neural network architecture which enables it to perform its described functions. For example, the ranking neural network 136 can include any appropriate types of neural networks layers (e.g., fully-connected layers, activation layers, attention layers, etc.) in any appropriate number (e.g., 5 layers, 10 layers, or 20 layers) and connected in any appropriate configuration (e.g., as a linear sequence of layers).

In some implementations, the ranking neural network 136 can be initialized using a base language model that has been pre-trained using unsupervised learning and then fine-tuned, through fine-tuning, on a custom dataset that includes question-document snippet pairs with relevance annotations. For example, the ranking neural network 136 can be initialized using the base language model described in Touvron, Hugo, et al. "Llama 2: Open foundation and fine-tuned chat models." arXiv preprint arXiv:2307.09288 (2023).

That is, the ranking neural network 136 can start with the same architecture and weights as (at least some part of) the base language model which has been trained on a corpus of text to perform one or more language modeling tasks that do not require labeled training examples, and then trained on custom data to learn fine-tuned weights based on optimizing a fine-tuning objective function, e.g., a supervised learning objective function. For example, the custom data can include a plurality of ranking training pairs. Each ranking training pair (i) includes a medical question and a document snippet and (ii) is associated with a ground truth score for each of the plurality of different levels of relevance.

After having performed the two-stage process to retrieve the subset of the document snippets, the medical question answering system 100 incorporates the subset of the document snippets into the prompt 118 and then causes the generative neural network 120 to generate the answer 126 to the medical question 102 based on processing the prompt 118.

The answer 126 to the medical question 102 will thus include an output sequence of tokens that is generated by the generative neural network 120 based on processing the prompt 118 that is represented as an input sequence of tokens.

In some implementations, the answer 126 includes a citation listing of the medical documents from which the subset of the plurality of document snippets are obtained. In some implementations, the answer 126 includes data identifying a rationale for the medical documents being cited. For example, the rationale can include, for each document snippet in the subset of document snippets, one or more of: a similarity explanation, an impact explanation, or a recency explanation.

For example, in response to a medical question, "What are health risks associated with GLP-1 receptor agonists like Ozempic and Mounjaro?" the medical question answering system 100 can generate an answer that includes:

Glucagon-like peptide-1 receptor agonists (GLP-1 RAs) such as semaglutide (Ozempic) and tirzepatide (Mounjaro) are associated with several health risks. The most common adverse events are gastrointestinal (GI) in nature, including nausea, vomiting, diarrhea, and abdominal pain.[1-2] There is also a risk of pancreatitis and biliary disease.[1]. . .

REFERENCES

1. GLP-1 Agonists: A Review for Emergency Clinicians.
   Long B, Pelletier J, Koyfman A, Bridwell RE.
   The American Journal of Emergency Medicine. 2024; 78:89-94. doi:10.1016/j.ajem.2024. 01.010.
   New Research
2. Gucagon-Like Peptide-1 Receptor Agonists Associated Gastrointestinal Adverse Events:
   A Cross-Sectional Analysis of the National Institutes of Health All of Us Cohort.
   Aldhaleei WA, Abegaz TM, Bhagavathula AS.
   Pharmaceuticals (Basel, Switzerland). 2024; 17(2):199. doi:10.3390/ph17020199.
   New Research In this example, the group of tokens that begin with "Glucagon-like" and end with "biliary disease" represents the answer to the question, where "[1]" and "[1-2]" are tokens that represent in-context citation marks, and the group of tokens below "References" represents a citation listing of medical documents that include the subset of the plurality of document snippets, where "New Research" are tokens that represent a rationale for the medical documents being cited (in this example because they are published within the predetermined period of time, e.g., with the past week, past month, or past year, from which the question is received). If available, the publication dates may be stored as metadata in association with the medical documents in the medical database. In other examples, the rationale for the medical documents could be a different rationale, e.g., a similarity explanation or an impact explanation.

The similarity explanation is based on the medical question embedding and the document snippet embeddings generated using the embedding model neural network. For example, if the similarity measure between the document snippet embedding for a particular document snippet and the medical question embedding of the medical question satisfies a predetermined threshold (e.g., a distance threshold in an embedding space), then the answer to the medical question can include tokens "Highly Relevant" as part of the citation listing to highlight the similarity between a source medical document that has the particular document snippet and the medical question.

The impact explanation is based on citation metrics of a source medical document to quantify the impact of the source medical document in the research community. If the source medical document is published in a journal that is above the $90^{th}$ or 95th percentile of impact factor, then the answer to the medical question can include tokens "Leading Journal" or "Top Journal" as part of the citation listing to highlight the impact of the source medical document. If available, the impact factors of the journal may be stored as metadata in association with the medical documents in the medical database.

In some implementations, the medical question answering system 100 can use the same generative neural network to generate multiple different candidate answers in response to the medical question. For example, when the generative neural network 120 is configured as an auto-regressive language model, some implementations of the medical question answering system 100 can do this by using beam search decoding from score distributions generated by the generative neural network 120, using a Sample-and-Rank decoding strategy, or using another decoding strategy that leverages the auto-regressive nature of the generative neural network 120.

The medical question answering system 100 can then select, from among the multiple different candidate answers, one or more selected candidate answers as the final answer 126 in response to the medical question 102 to output for presentation on a display of a user device.

For example, the selection can be made based on using an evaluation model that implements an evaluation function. As another example, the selection can be made by using the generative neural network 120 to "discriminate" between the generated candidate answers to determine which candidate answer, if any, to provide in response to the medical question 102.

In some implementations, after having obtained question data representing a medical question 102, the medical question answering system 100 can generate different prompts 118 based on the same medical question 102 and then, for each different prompt, generate a candidate answer by using the generative neural network 120 to process the prompt 118. For example, different prompts 118 can include document snippets selected from different types of medical documents stored in the medical database 150.

Figure 6:
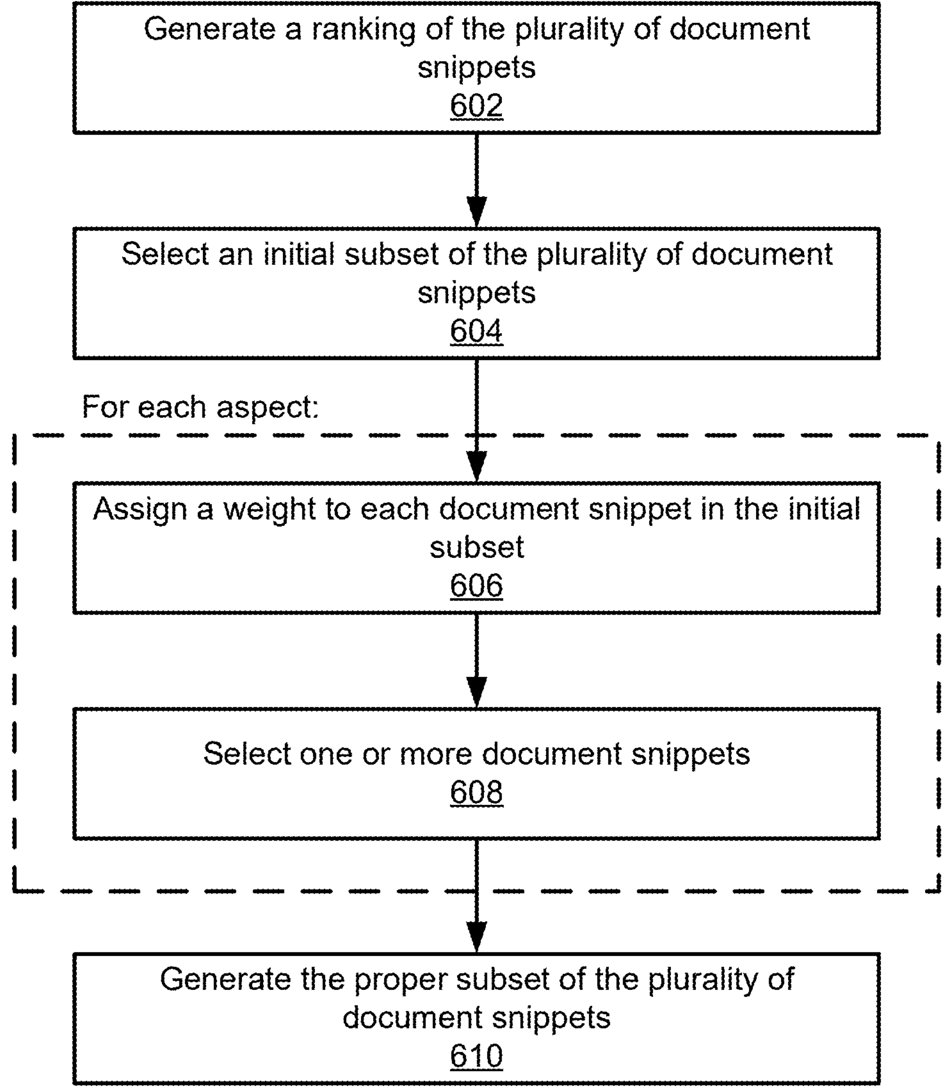
FIG. 6 is a flow diagram of sub-steps of another one of the steps of the process of FIG. 4 for selecting a proper subset of a plurality of document snippets.

For example, will be described further below with reference to FIGS. 6-7, some implementations of the medical question answering system 100 can generate a first prompt that includes document snippets obtained only from one or more clinical practice guideline documents stored in the medical database 150 (and not from any other medical documents stored in the medical database) and a second prompt that includes document snippets obtained from the other medical documents stored in the medical database 150.

In this example, the first answer generated by the generative neural network 120 in response to the first prompt can be presented using a first user interface element that is different from a second user interface element that presents a second answer generated by the generative neural network 120 in response to the second prompt.

After having generated an answer 126 and prior to providing the generated answer for presentation on the display, the medical question answering system 100 can use a quality assurance engine 140 to quality check the answer 126 generated by using the generative neural network 120 to ensure the quality of the answer.

In some implementations, the quality assurance engine 140 can use a hallucination detection neural network that is configured to process a hallucination detection input that includes the answer 126 and the subset of the document snippets to generate one or more hallucination detection outputs that can be used by the quality assurance engine 140 to determine whether the answer 126 contains any hallucination content, i.e., to determine whether the generative neural network 120 synthesizes any non-existent, distorted, or inaccurate information.

The hallucination detection neural network can have any appropriate neural network architecture which enables it to perform its described functions. For example, the hallucination detection neural network can include any appropriate types of neural networks layers (e.g., fully-connected layers, embedding layers, attention layers, etc.) in any appropriate number (e.g., 5 layers, 10 layers, or 20 layers) and connected in any appropriate configuration (e.g., as a linear sequence of layers).

In some implementations, the hallucination detection neural network can be initialized using a base language model that has been pre-trained using unsupervised learning and then fine-tuned, e.g., through supervised fine-tuning, on a custom dataset that includes a plurality of hallucination detection training examples.

For example, each hallucination detection training example can include a hallucination detection training input and a hallucination detection target output. The hallucination detection training input can include a first sequence of text and a second sequence of text. The hallucination detection target output can indicate whether the first sequence of text contains content that is in contradiction to the content contained in the second sequence of text, whether the first sequence of text contains content that is relevant to, similar to, or in support of, the content contained in the second sequence of text, and so on.

In practice the hallucination detection can be performed at various levels, e.g., at sentence level, paragraph level, and so on. For example, the one or more hallucination detection outputs can include a hallucination detection output that indicate whether there exists any contradiction between (i) each sentence or each paragraph included in the response generated by the generative neural network 120 from processing the prompt 118 and (ii) the subset of the document snippets.

As another example, the one or more hallucination detection outputs can include a hallucination detection output that indicate whether at least one document snippet in the subset of the document snippets supports each sentence or each paragraph included in the response generated by the generative neural network from processing the prompt.

In these implementations, in response to determining that a contradiction or a lack of support by the document snippets exists in an answer, the medical question answering system 100 can withhold providing the answer to the user. Instead, the system 100 can augment, e.g., apply a modification or correction to, the answer generated by the generative neural network 120 to generate an augmented answer. As another example, the system 100 can re-run the to generate another answer.

Once the answer 126 generated by the generative neural network 120 has been quality checked by the quality assurance engine 140, the medical question answering system 100 can provide the answer 126 to the user. Additionally or alternatively, the system 100 can provide the answer 126 to another system for further processing, or store the answer 126 in a storage device for some future purpose.

For example, the medical question answering system 100 can provide the answer 126 for presentation in a user interface of a user device, e.g., the user device through which the user submitted the medical question 102.

As another example, the medical question answering system 100 can be implemented as part of or can be in communication with a digital assistant device, e.g., a mobile device, a smartwatch or other wearable device, or a smart speaker device, and the digital assistant device can provide the answer 126 to the user, e.g., by generating speech representing the answer 126 and playing back the speech to the user over a speaker.

Figure 4:
FIG. 4 is a flow diagram of an example process for generating an answer to a medical question.
Figure 4:
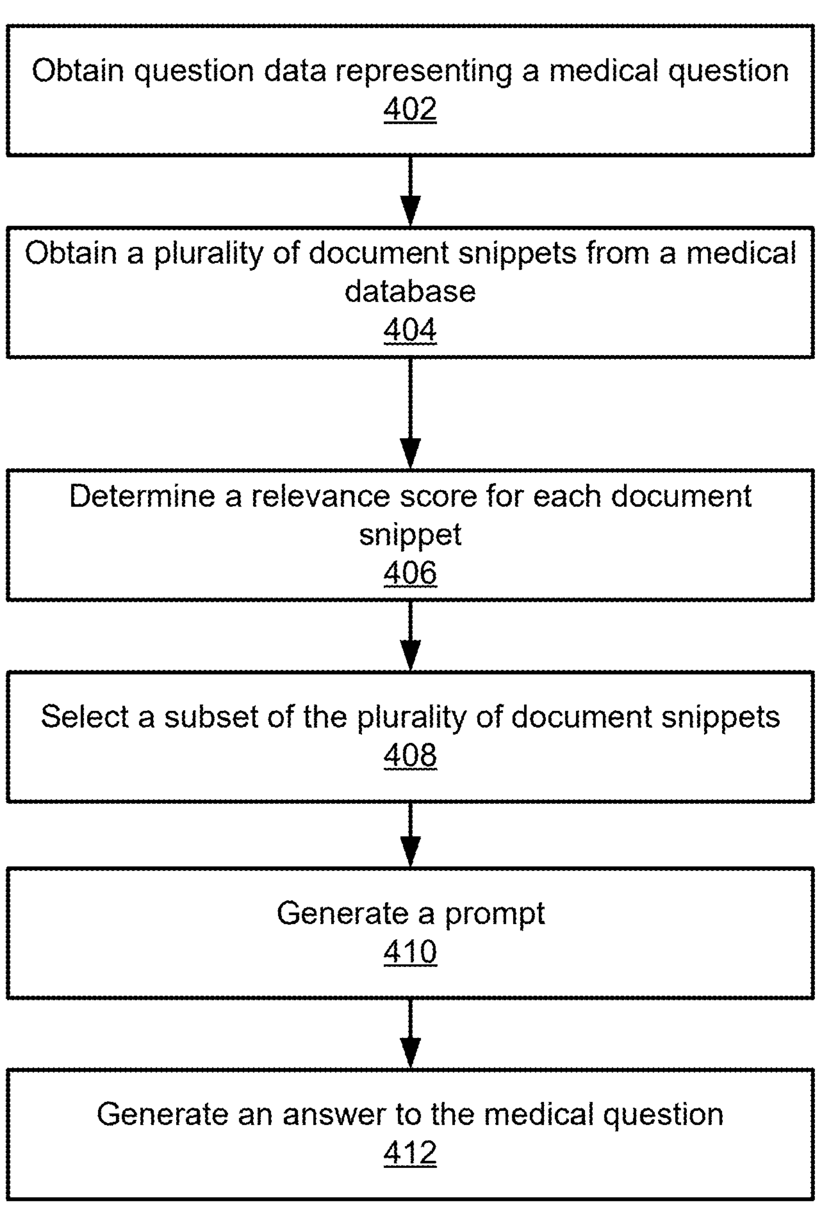
Figure 5:
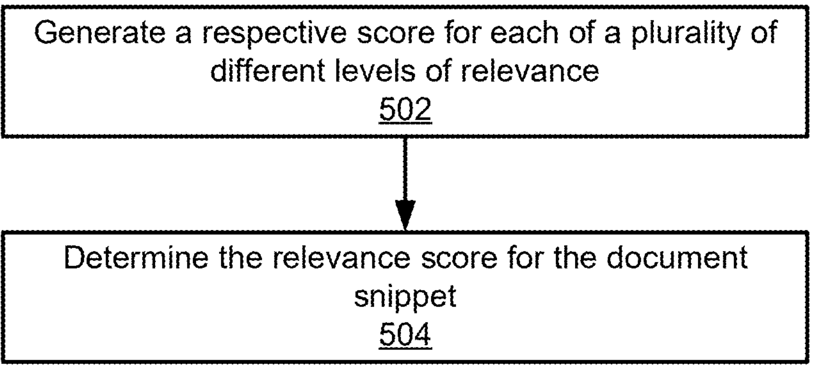
FIG. 5 is a flow diagram of sub-steps of one of the steps of the process of FIG. 4 for determining relevance scores for a document snippet.

FIG. 4 is a flow diagram of an example process 400 for generating an answer to a medical question. For convenience, the process 400 will be described as being performed by a system of one or more computers located in one or more locations. For example, a medical question answering system, e.g., the medical question answering system 100 of FIG. 1, appropriately programmed in accordance with this specification can perform the process 400.

The system obtains question data representing a medical question (step 402), e.g., from a user through a user interface.

The system obtains a plurality of document snippets from a medical database that stores medical documents (step 404). Step 404 can correspond to the initial retrieval step in the two-stage search process.

To obtain the plurality of document snippets, the system obtains an embedding of the medical question (a "medical question embedding") that has been generated by the embedding model based on the medical question and, for each of the document snippets stored in the medical database, an embedding of document snippet (a "document snippet embedding") that has been generated by the embedding model based on the document snippet. In some implementations, the embeddings of the document snippets can be pre-computed and stored in a data storage to allow them to be reused at each iteration of process 400 to reduce runtime latency.

The system then searches for the k document snippet embeddings that are most similar to the medical question embedding according to some similarity measure. K can generally be any positive integer, i.e., any integer greater than or equal to one, but is generally much smaller than the total number N of the document snippets stored in the medical database. In effect the system performs a search in the medical database to retrieve the plurality of document snippets that correspond respectively to the k document snippet embeddings.

For some similarity measures, e.g., Manhattan distance, Euclidean distance, or other distance measures, the most similar document snippet embeddings are those that are closest to the medical question embedding (have the smallest similarity measure with the medical question embedding). For some other similarity measures, e.g., inner product, the most similar document snippet embeddings are those that have the largest similarity measure with the medical question embedding.

For each document snippet in the plurality of document snippets, the system determines a relevance score for the document snippet by using a ranking neural network based on the document snippet and the medical question (step 406). Then, the system selects, based at least in part on the relevance scores that have been determined for the plurality of document snippets, a proper subset of the plurality of document snippets (step 408). Steps 406-408 can correspond to the re-ranking step in the two-stage search process. By performing the re-ranking step, the system further reduces the plurality of document snippets to the proper subset of the plurality of document snippets.

Determining the relevance scores for the document snippets is described below in FIG. 5, which is a flow diagram of sub-steps 502-504 of step 406 of the process 400 of FIG. 4.

For each document snippet in the plurality of document snippets, the system processes, using the ranking neural network, an input that includes the medical question and the document snippet to generate a respective score for each of a plurality of different levels of relevance (step 502). For each level of relevance, the respective score indicates a probability that a relevance between the medical question and the document snippet has the level of relevance.

For example, for each document snippet in the plurality of document snippets, the output of the ranking neural network can include:

P(A|question, snippet), P(B|question, snippet), . . . P(F|question, snippet)

where A, B, . . . F are tokens that represent the different levels of relevance. For example, A represent the highest level of relevance (namely the document question is very relevant the question), B represent the second highest level of relevance (namely the document question is somewhat relevant the question, and so on. In other examples, there can be more or fewer different levels of relevance. The different levels of relevance can also be represented using different tokens.

For each document snippet in the plurality of document snippets, the system determines the relevance score for the document snippet based on output of the ranking neural network, i.e., based on the respective scores generated by the ranking neural network for the plurality of levels of relevance (step 504).

For example, the relevance score can be determined as a linear combination of the scores:

X_0*P(A|question, snippet)+X_1*P(B|question, snippet)+ . . . X_6*P(F|question, snippet), where X_0, X_1, . . . X_6 are predetermined weights which may be, for example, tunable hyperparameters of the system.

Selecting the proper subset of the plurality of document snippets based at least in part on the relevance scores is described below in FIG. 6, which is a flow diagram of sub-steps 602-608 of step 408 of the process 400 of FIG. 4.

The system generates a ranking of the plurality of document snippets based on the relevance score that has been determined for each document snippet by using the ranking neural network (step 602). For example, the plurality of document snippets are arranged in the ranking where the document snippet with the highest score is placed on top of the ranking and the document snippet with the lowest score is placed on bottom of the ranking.

The system selects, as an initial subset of the plurality of document snippets, highest scored document snippets that have the highest relevance scores in accordance with the ranking (step 604). The initial subset of the plurality of document snippets includes document snippets that have the highest relevance scores from among the plurality of document snippets. For example, the system can select the document snippets that are placed on the top of the ranking.

For each of a plurality of aspects, the system assigns a weight to each document snippet in the initial subset of the plurality of document snippets with respect to the aspect (step 606), and then selects, from the document snippets in the initial subset of the plurality of document snippets, one or more document snippets based on the respective weight assigned to each document snippet (step 608), e.g., one or more document snippets that have the highest weights. The weights assigned to the same document snippet can be different for different aspects.

For example, the plurality of aspects can include one or more of: a recency of a source medical document that includes the document snippet (i.e., a difference between the publication date and the date on which the medical question is received), a quality of a provider of the medical document (e.g., an impact factor of a journal in which the medical document is published), or a relevancy between a user who submitted the medical question and an author of the medical document (e.g., an affiliation or other relationship). As a particular example of this, for a given medical document, the system can generate a higher weight for the relevancy if the user who submitted the medical question is also the author of the given medical document.

In some implementations, the system selects a same fixed number of document snippets based on the respective weights for each of the plurality of aspects, whereas, in other implementations, the system selects a different number of document snippets based on the respective weights for each of the plurality of aspects, i.e., the system may select more document snippets for one aspect than document snippets for another aspect.

The system combines, e.g., joins, the one or more document snippets that have been selected for each of the plurality of aspects to generate a combined set of document snippets (step 610). The combined set of document snippets can then be used as the proper subset of the plurality of document snippets. In some implementations, the system applies further processing, e.g., semantic filtering, deduplication, or both, to the combined set of document snippets to generate the subset of the plurality of document snippets.

The system generates a prompt that includes at least the medical question and the proper subset of the plurality of document snippets (step 410). Optionally, the prompt also includes additional data, e.g., one or more of the types of data (or metadata) that have been mentioned above with reference to FIG. 1.

The system causes a generative neural network to process, as input, the prompt to generate, as output, an answer to the medical question (step 412). For example, the answer can be represented as an output sequence that includes tokens selected from a vocabulary, and the generative neural network can auto-regressively generate the answer by generating the tokens that make up the output sequence one after another, conditioned on any tokens that have already been generated in the output sequence.

Figure 7:
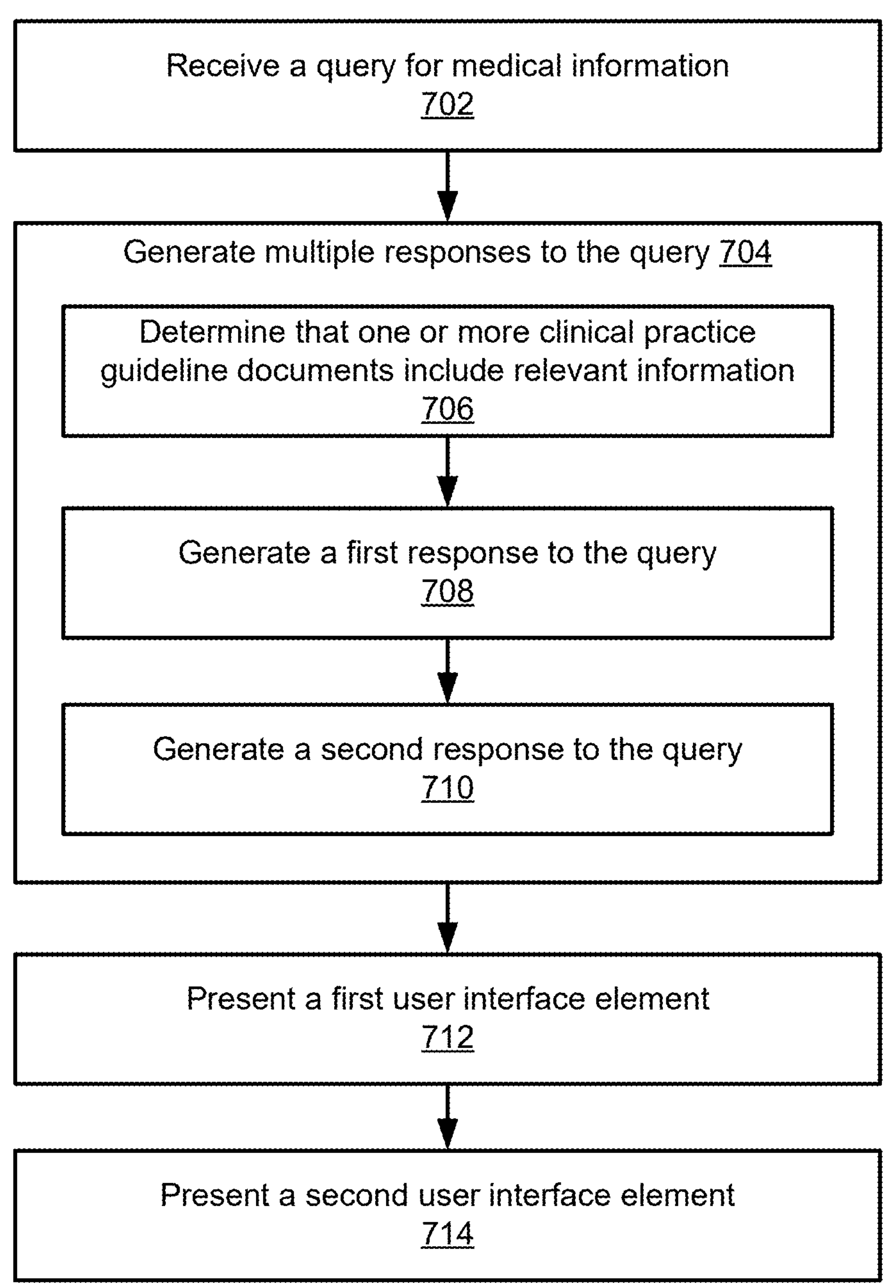
FIG. 7 is a flow diagram of an example process for generating a response to a query from a user.

FIG. 7 is a flow diagram of an example process 700 for generating a response to a query from a user. For convenience, the process 700 will be described as being performed by a system of one or more computers located in one or more locations. For example, a medical question answering system, e.g., the medical question answering system 100 of FIG. 1, appropriately programmed in accordance with this specification can perform the process 700.

The system receives, from a user and by way of a user interface presented to the user on a display of a user device, a query for medical information (step 702).

The system generates multiple responses to the query received from the user by automatically retrieving and parsing data from a corpus of medical documents stored in a medical database using generative neural network (step 704). The multiple responses can include a first response and a second response.

The generative neural network is configured to generate a response based on processing a prompt that is generated by the system based on the query and data, e.g., document snippets, retrieved from the corpus of medical documents. In particular, the system generates different prompts based on the query, and then processes each different prompt using the same generative neural network to generate a respective response to the prompt.

As part of the generation of the first response, the system determines, based on an automated search of the corpus of medical documents, that one or more clinical practice guideline documents from the corpus of medical documents document include information that is responsive or relevant to the query (step 706).

In some implementations, he automated search can be a two-stage process that is performed by using an embedding model and a ranking neural network, as discussed above. For example, the document snippets selected in the re-ranking step each have a similarity measure with respect to the medical question embedding that satisfies a similarity threshold (e.g., a distance threshold in an embedding space).

In some other implementations, the automated search can be a one-stage process that is performed by using the embedding model. The one-stage process can include the initial retrieval step, but excludes the re-ranking step. For example, the system can select a document snippet from the document snippets stored in the medical database according to the similarity measure. The selected document snippet has a similarity measure with respect to the medical question embedding that satisfies the similarity threshold.

In response to determining that one or more clinical practice guideline documents include information that is responsive or relevant to the query, the system generates a first prompt that includes (i) the query for medical information and (ii) data extracted from the one or more clinical practice guideline documents, e.g., one or more document snippets included in the one or more clinical practice guideline documents, and then processes the first prompt using the generative neural network to generate the first response to the query (step 708).

In particular, the first prompt includes data extracted from the one or more clinical practice guideline documents, but excludes, i.e., does not include, any data extracted from other medical documents that might be stored in the medical database and that are not clinical practice guideline documents.

For example, the first prompt does not include any data extracted from clinical trial documents. Nor does the first prompt include any data extracted from medical label documents. Nor does the first prompt include any data extracted from agency communication documents. Nor does the first prompt include any data extracted from clinical research documents.

The system generates a second prompt that includes at least (i) the query for medical information and (ii) data extracted from one or more other medical documents that are not clinical practice guideline documents, e.g., one or more document snippets included in the one or more other medical documents, and then processes the second prompt using the generative neural network to generate the second response to the query (step 710). In some implementations, the second prompt can also include the first prompt, the first response, or both.

For example, the one or more other medical documents can have been retrieved in the same automated search that also retrieved the one or more clinical practice guideline documents, or in a separate automated search through the medical database. Generally, the one or more other medical documents are distinct from the one or more clinical practice guideline documents, e.g., the one or more other medical documents can include one or more clinical trial documents, one or more medical label documents, or both.

In implementations the system can generate the first response to the query and the second response to the query by making separate calls to the generative neural network. In other words, the system can make a first call to the generative neural network to cause the generative neural network to generate the first response to the query based on the first prompt. Then, after the generative neural network has generated the first response in response to the first call, the system can make a second call to the generative neural network to cause the generative neural network to generate the second response to the query based on the second prompt.

The system presents a first user interface element by way of the user interface and on the display of the user device (step 712). The first user interface element presents the first response that is generated based on the clinical practice guideline documents but not on any other medical documents.

The first user interface element visually highlights that the first response is derived only from clinical practice guideline documents (and not from any other medical documents that are not clinical practice guideline documents) and identifies the one or more clinical practice guideline document that were processed to generate the first response.

The system presents a second user interface element by way of the user interface and on the display of the user device (step 714). The second user interface element presents the second response generated based at least in part on other medical documents that are not clinical practice guideline documents. That is, the second user interface element is presented within the same user interface, but lacks the visual indication that the second response is derived only from clinical practice guideline documents.

Figure 8:
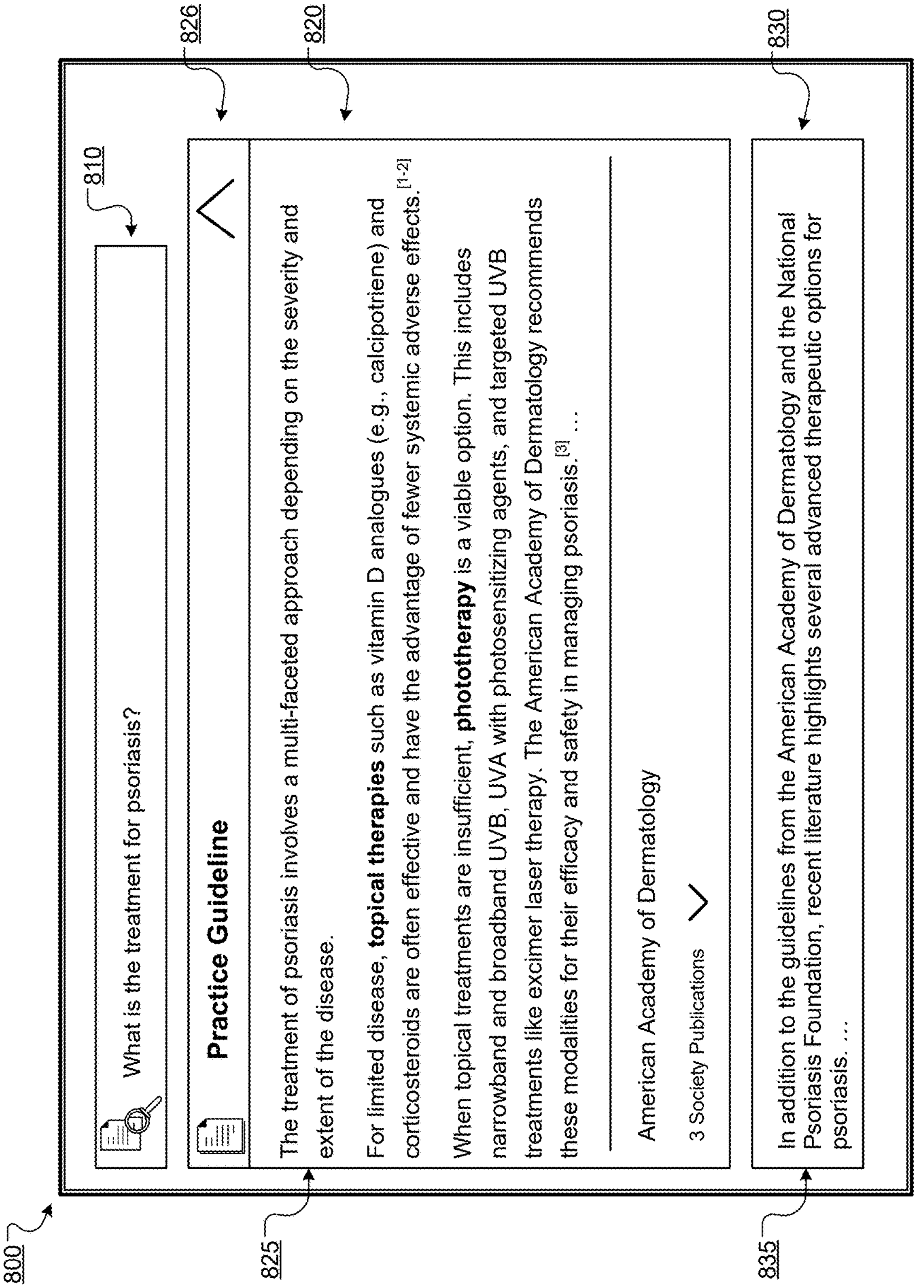
FIG. 8 is an illustration of example of a user interface.

FIG. 8 is an illustration of example of a user interface 800.

The user interface 800 presents an entry window 810 for a user to enter a query. In the example of FIG. 8, the user has entered "What is the treatment for psoriasis?" and in response, the user interface 800 presents a first user interface element 820 within which a first response 825 "The treatment of psoriasis involves a multi-faceted approach depending on the severity and extent of the disease . . . " can be displayed, and also presents a second user interface element 830 within which a second response 835 "In addition to the guidelines from the American Academy of Dermatology and the National Psoriasis Foundation . . . " can be displayed.

In the example of FIG. 8, the first user interface element 820 is presented on top of and temporally before the second user interface element 830 within the user interface 800. Moreover, in the example of FIG. 8, the first user interface element 820 is a walled garden environment that is presented within the user interface 800. The first response 825 that is generated based on the clinical practice guideline documents but not on any other medical documents is presented within the walled garden environment.

Also presented within the walled garden environment is a citation listing of the one or more clinical practice guideline documents (which include three clinical practice guideline documents published by American Academy Dermatology in the example of FIG. 8) based on which the first response 825 is generated.

Optionally, the first user interface element 820 can include a header 826 "Practice Guideline" which indicates the first response 825 is generated based on the clinical practice guideline documents but not on any other medical documents.

Optionally, the first user interface element 820 can be displayed as a short summary that is expandable upon selection (e.g., double click, hover, etc.) to display a more thorough presentation.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers for reducing risk of hallucination and reducing latency when generating responses to medical questions using a generative neural network, the method comprising:

receiving, from a user and by way of a user interface presented to the user on a display of a user device, a medical question;

generating multiple answers to the medical question from the user by automatically retrieving and parsing data from a corpus of documents, comprising:

generating, by using an embedding model, a medical question embedding for the medical question;

performing an automated search to identify, from the corpus of documents, document snippets that include information that is relevant to the medical question, wherein performing the automated search comprises:

prior to receiving the medical question:

generating, by using the embedding model, a document snippet embedding for each document snippet of at least a subset of the document snippets, wherein the embedding model has been trained based on generating more training medical question embeddings than training document snippet embeddings during training, and storing the document snippet embedding for each document snippet of at least the subset of the document snippets, and after receiving the medical question, performing an embedding-based search that uses the medical question embedding and the document snippet embedding for each document snippet of at least the subset of the document snippets;

partitioning the identified document snippets into first document snippets that are obtained from one or more clinical practice guideline documents and second document snippets that are obtained from one or more other documents that are not clinical practice guideline documents;

generating a first prompt by including (i) the medical question and (ii) the first document snippets that are obtained from the one or more clinical practice guideline documents, excluding the second document snippets that are obtained from the one or more other documents that are not clinical practice guideline documents;

making a first call to a generative neural network to cause the generative neural network to generate a first answer to the medical question based on processing the first prompt that includes (i) the medical question and (ii) the first document snippets that are obtained from the one or more clinical practice guideline documents but excludes the second document snippets that are obtained from the one or more other documents that are not clinical practice guideline documents, such that the generative neural network generates the first answer without being conditioned on the second document snippets that are obtained from the one or more other documents that are not clinical practice guideline documents; and generating a second prompt by including (i) the medical question, (ii) the first document snippets that are obtained from the one or more clinical practice guideline documents, and (iii) the second document snippets that are obtained from the one or more other documents that are not clinical practice guideline documents;

making a second call to the generative neural network to cause the generative neural network to generate a second answer to the medical question based on processing a second prompt that includes (i) the medical question, (ii) the first document snippets that are obtained from the one or more clinical practice guideline documents, and (iii) the second document snippets that are obtained from the one or more other documents that are not clinical practice guideline documents, such that the generative neural network generates the second answer being conditioned at least on the second document snippets that are obtained from the one or more other documents that are not clinical practice guideline documents; and presenting, by way of the user interface and on the display of the user device:

a first user interface element that presents the first answer generated by the generative neural network in response to the first call, wherein the first user interface element visually highlights that the first answer is derived only from clinical practice guideline documents and identifies the one or more clinical practice guideline document that were processed by the generative neural network to generate the first answer; and a second user interface element that presents the second answer generated by the generative neural network in response to the second call.

2. The method of claim 1, wherein the first user interface element is presented on top of and temporally before the second user interface element within the user interface.

3. The method of claim 1, wherein the first user interface element comprises a walled garden environment presented within the user interface, and wherein the first response generated based only on the clinical practice guideline documents is presented within the walled garden environment.

4. The method of claim 1, wherein the first user interface element comprises a header that indicates the first response is generated based only on clinical practice guideline documents.

5. The method of claim 1, wherein making the second call to the generative neural network comprises making the second call after the generative neural network has generated the first response in response to the first call.

6. The method of claim 1, wherein the second prompt comprises the first response generated by the generative neural network in response to the first call.

7. A system comprising:

one or more computers; and one or more storage devices communicatively coupled to the one or more computers, wherein the one or more storage devices store instructions that, when executed by the one or more computers, cause the one or more computers to perform operations for reducing risk of hallucination and reducing latency when generating responses to medical questions using a generative neural network, the operations comprising:

receiving, from a user and by way of a user interface presented to the user on a display of a user device, a medical question;

generating multiple answers to the medical question from the user by automatically retrieving and parsing data from a corpus of documents, comprising:

generating, by using an embedding model, a medical question embedding for the medical question;

performing an automated search to identify, from the corpus of documents, document snippets that include information that is relevant to the medical question, wherein performing the automated search comprises:

prior to receiving the medical question:

generating, by using the embedding model, a document snippet embedding for each document snippet of at least a subset of the document snippets, wherein the embedding model has been trained based on generating more training medical question embeddings than training document snippet embeddings during training, and storing the document snippet embedding for each document snippet of at least the subset of the document snippets, and after receiving the medical question, performing an embedding-based search that uses the medical question embedding and the document snippet embedding for each document snippet of at least the subset of the document snippets;

partitioning the identified document snippets into first document snippets that are obtained from one or more clinical practice guideline documents and second document snippets that are obtained from one or more other documents that are not clinical practice guideline documents;

generating a first prompt by including (i) the medical question and (ii) the first document snippets that are obtained from the one or more clinical practice guideline documents, excluding the second document snippets that are obtained from the one or more other documents that are not clinical practice guideline documents;

making a first call to a generative neural network to cause the generative neural network to generate a first answer to the medical question based on processing the first prompt that includes (i) the medical question and (ii) the first document snippets that are obtained from the one or more clinical practice guideline documents but excludes the second document snippets that are obtained from the one or more other documents that are not clinical practice guideline documents, such that the generative neural network generates the first answer without being conditioned on the second document snippets that are obtained from the one or more other documents that are not clinical practice guideline documents; and generating a second prompt by including (i) the medical question, (ii) the first document snippets that are obtained from the one or more clinical practice guideline documents, and (iii) the second document snippets that are obtained from the one or more other documents that are not clinical practice guideline documents;

making a second call to the generative neural network to cause the generative neural network to generate a second answer to the medical question based on processing a second prompt that includes (i) the medical question, (ii) the first document snippets that are obtained from the one or more clinical practice guideline documents, and (iii) the second document snippets that are obtained from the one or more other documents that are not clinical practice guideline documents, such that the generative neural network generates the second answer being conditioned at least on the second document snippets that are obtained from the one or more other documents that are not clinical practice guideline documents; and presenting, by way of the user interface and on the display of the user device:

a first user interface element that presents the first answer generated by the generative neural network in response to the first call, wherein the first user interface element visually highlights that the first answer is derived only from clinical practice guideline documents and identifies the one or more clinical practice guideline document that were processed by the generative neural network to generate the first answer; and a second user interface element that presents the second answer generated by the generative neural network in response to the second call.

8. The system of claim 7, wherein the first user interface element is presented on top of and temporally before the second user interface element within the user interface.

9. The system of claim 7, wherein the first user interface element comprises a walled garden environment presented within the user interface, and wherein the first response generated based only on the clinical practice guideline documents is presented within the walled garden environment.

10. The system of claim 7, wherein the first user interface element comprises a header that indicates the first response is generated based only on clinical practice guideline documents.

11. The system of claim 7, wherein making the second call to the generative neural network comprises making the second call after the generative neural network has generated the first response in response to the first call.

12. The system of claim 7, wherein the second prompt comprises the first response generated by the generative neural network in response to the first call.

13. One or more non-transitory computer storage media storing instructions that when executed by one or more computers cause the one or more computers to perform operations for reducing risk of hallucination and reducing latency when generating responses to medical questions using a generative neural network, the operations comprising:

receiving, from a user and by way of a user interface presented to the user on a display of a user device, a medical question;

generating multiple answers to the medical question from the user by automatically retrieving and parsing data from a corpus of documents, comprising:

generating, by using an embedding model, a medical question embedding for the medical question;

performing an automated search to identify, from the corpus of documents, document snippets that include information that is relevant to the medical question, wherein performing the automated search comprises:

prior to receiving the medical question:

generating, by using the embedding model, a document snippet embedding for each document snippet of at least a subset of the document snippets, wherein the embedding model has been trained based on generating more training medical question embeddings than training document snippet embeddings during training, and storing the document snippet embedding for each document snippet of at least the subset of the document snippets, and after receiving the medical question, performing an embedding-based search that uses the medical question embedding and the document snippet embedding for each document snippet of at least the subset of the document snippets;

partitioning the identified document snippets into first document snippets that are obtained from one or more clinical practice guideline documents and second document snippets that are obtained from one or more other documents that are not clinical practice guideline documents;

generating a first prompt by including (i) the medical question and (ii) the first document snippets that are obtained from the one or more clinical practice guideline documents, excluding the second document snippets that are obtained from the one or more other documents that are not clinical practice guideline documents;

making a first call to a generative neural network to cause the generative neural network to generate a first answer to the medical question based on processing the first prompt that includes (i) the medical question and (ii) the first document snippets that are obtained from the one or more clinical practice guideline documents but excludes the second document snippets that are obtained from the one or more other documents that are not clinical practice guideline documents, such that the generative neural network generates the first answer without being conditioned on the second document snippets that are obtained from the one or more other documents that are not clinical practice guideline documents; and generating a second prompt by including (i) the medical question, (ii) the first document snippets that are obtained from the one or more clinical practice guideline documents, and (iii) the second document snippets that are obtained from the one or more other documents that are not clinical practice guideline documents;

making a second call to the generative neural network to cause the generative neural network to generate a second answer to the medical question based on processing a second prompt that includes (i) the medical question, (ii) the first document snippets that are obtained from the one or more clinical practice guideline documents, and (iii) the second document snippets that are obtained from the one or more other documents that are not clinical practice guideline documents, such that the generative neural network generates the second answer being conditioned at least on the second document snippets that are obtained from the one or more other documents that are not clinical practice guideline documents; and presenting, by way of the user interface and on the display of the user device:

a first user interface element that presents the first answer generated by the generative neural network in response to the first call, wherein the first user interface element visually highlights that the first answer is derived only from clinical practice guideline documents and identifies the one or more clinical practice guideline document that were processed by the generative neural network to generate the first answer; and a second user interface element that presents the second answer generated by the generative neural network in response to the second call.

14. The computer storage media of claim 13, wherein the first user interface element is presented on top of and temporally before the second user interface element within the user interface.

15. The computer storage media of claim 13, wherein the first user interface element comprises a walled garden environment presented within the user interface, and wherein the first response generated based only on the clinical practice guideline documents is presented within the walled garden environment.

16. The computer storage media of claim 13, wherein making the second call to the generative neural network comprises making the second call after the generative neural network has generated the first response in response to the first call.

17. The computer storage media of claim 13, wherein the second prompt comprises the first response generated by the generative neural network in response to the first call.

* * * * *